US012678431B2

(12) United States Patent
Yamada et al.

(10) Patent No.: US 12,678,431 B2
(45) Date of Patent: Jul. 14, 2026

(54) PHARMACEUTICAL COMPOSITION FOR TREATMENT OF DEMENTIA AND CEREBROVASCULAR DISORDERS

(71) Applicants: Ken-ichi Yamada, Fukuoka (JP); FUSO PHARMACEUTICAL INDUSTRIES, LTD., Osaka (JP)

(72) Inventors: Ken-ichi Yamada, Fukuoka (JP); Keiichi Yamamoto, Osaka (JP)

(73) Assignee: FUSO PHARMACEUTICAL INDUSTRIES, LTD., Osaka (JP)

( * ) Notice: Subject to any disclaimer, the term of this patent is extended or adjusted under 35 U.S.C. 154(b) by 989 days.

(21) Appl. No.: 17/421,921

(22) PCT Filed: Jan. 9, 2020

(86) PCT No.: PCT/JP2020/000510

§ 371 (c)(1),
(2) Date: Jul. 9, 2021

(87) PCT Pub. No.: WO2020/145359

PCT Pub. Date: Jul. 16, 2020

(65) Prior Publication Data

US 2022/0023283 A1 Jan. 27, 2022

Related U.S. Application Data

(60) Provisional application No. 62/790,305, filed on Jan. 9, 2019.

(51) Int. Cl.

| | |
|---|---|
| ***A61K 31/47*** | (2006.01) |
| ***A23L 2/52*** | (2006.01) |
| ***A23L 33/00*** | (2016.01) |
| ***A23L 33/10*** | (2016.01) |
| ***A61K 31/137*** | (2006.01) |
| ***A61K 31/197*** | (2006.01) |
| ***A61K 31/198*** | (2006.01) |
| ***A61K 31/4045*** | (2006.01) |
| ***A61K 31/407*** | (2006.01) |
| ***A61K 31/4439*** | (2006.01) |
| ***A61K 31/473*** | (2006.01) |
| ***A61K 31/551*** | (2006.01) |
| ***A61P 9/10*** | (2006.01) |
| ***A61P 25/28*** | (2006.01) |

(52) U.S. Cl.

CPC ................ *A61K 31/47* (2013.01); *A23L 2/52* (2013.01); *A23L 33/10* (2016.08); *A23L 33/40* (2016.08); *A61K 31/197* (2013.01); *A61P 25/28* (2018.01); *A23V 2002/00* (2013.01)

(58) Field of Classification Search

CPC .... A61K 31/47; A61K 31/197; A61K 31/137; A61K 31/4045; A61K 31/407; A61K 31/4439; A61K 31/198; A61K 31/473; A61K 31/551; A23L 2/52; A23L 33/10; A23L 33/40; A23L 33/00; A61P 25/28; A61P 9/10; A23V 2002/00

See application file for complete search history.

(56) References Cited

U.S. PATENT DOCUMENTS

| | | | | |
|---|---|---|---|---|
| 11,519,893 | B2 * | 12/2022 | Yamada | A61P 11/06 |
| 2004/0053851 | A1 | 3/2004 | Chabrier de Lassauniere | |
| 2007/0129350 | A1 | 6/2007 | Bruinsma | |
| 2019/0083549 | A1 | 3/2019 | Kobayashi et al. | |
| 2020/0158709 | A1 | 5/2020 | Yamada et al. | |

FOREIGN PATENT DOCUMENTS

| | | | |
|---|---|---|---|
| EP | 0872239 | A2 | 10/1998 |
| EP | 1181935 | | 2/2002 |
| JP | 2004-533937 | | 11/2004 |
| JP | 2004-533987 | | 11/2004 |
| JP | 2013-194007 | | 9/2013 |
| KR | 2013-0070371 | | 6/2013 |
| KR | 10-1730290 | B1 | 4/2017 |
| NO | 2019/009355 | | 1/2019 |
| WO | 03/004196 | | 1/2003 |
| WO | 2008/140449 | | 11/2008 |
| WO | 2017/209156 | | 12/2017 |

OTHER PUBLICATIONS

Gleeson MP, Hersey A, Montanari D, Overington J. Probing the links between in vitro potency, ADMET and physicochemical parameters. Nat Rev Drug Discov. Mar. 2011;10(3):197-208. doi: 10.1038/nrd3367. PMID: 21358739; PMCID: PMC6317702. (Year: 2011).*

Hu X, De Silva TM, Chen J, Faraci FM. Cerebral Vascular Disease and Neurovascular Injury in Ischemic Stroke. Circ Res. Feb. 3, 2017;120(3):449-471. doi: 10.1161/CIRCRESAHA.116.308427. PMID: 28154097; PMCID: PMC5313039. (Year: 2017).*

Abe M, Sou M, Matsuoka Y, Morimoto K, Yamada KI. Ethoxyquin, a Lipid Peroxidation Inhibitor, Has Protective Effects against White Matter Lesions in a Mouse Model of Chronic Cerebral Hypoperfusion. Biol Pharm Bull. 2024;47(1):104-111. doi: 10.1248/bpb.b23-00538. PMID: 38171771. (Year: 2024).*

(Continued)

*Primary Examiner* — Bruck Kifle
*Assistant Examiner* — Kevin S Martin
(74) *Attorney, Agent, or Firm* — HSML P.C.

(57) ABSTRACT

The disclosures as described herein a pharmaceutical composition for preventing or treating a cerebrovascular disorder or a vascular dementia, or suppressing a progression of the diseases in a subject in need of the treatment and so on, the composition comprising one or more compounds selected from the following group, and a pharmaceutically acceptable carrier; and a method using the same. A group consisting of apomorphine, eseroline, ethoxyquin, methyldopa, olanzapine, indapamide, and the others.

12 Claims, 5 Drawing Sheets

(56) References Cited

OTHER PUBLICATIONS

Merriam-Webster, Prevent, 2024, https://www.merriam-webster.com/dictionary/prevention (Year: 2024).*
Office Action issued for Chinese Patent Application No. 202080008310.1, Feb. 7, 2024, 17 pages including English translation.
The extended European Search Report of European Patent Application No. 20738052.8, Sep. 1, 2022, 11 pages.
Ebihara, Akio, "The behind story of antihypertensive drug development: Methyldopa", Journal of Blood Pressure, vol. 13, No. 8, 917-920; fig. 1, p. 920, left column, col. "4, Current status and future prospects of methyldopa"; English translation provided.
Peng, M. et al., "Blood pressure at age 60-65 versus age 70-75 and vascular dementia: a population based observational study", BMC Geriatrics, 2017, vol. 17, 252, abstract.
International Search Report of PCT/JP2020/000510, Mar. 24, 2020, 3 pages.
International Preliminary Report on Patentability of PCT/JP2020/000510, Jun. 16, 2021, 9 pages.
Office Action issued for Japanese Patent Application No. 2020-565210, Oct. 31, 2023, 9 pages with English translation.
Office Action and search report issued in the corresponding Chinese Patent Application No. 202080008310.1, May 18, 2023, 16 pages including English translation.
Wang Chengzhi, et al., "Prospective Studies of Effects of Imdapamide on Prognosis of Cerebrovascular Accident and Vascular Dementia", "Chinese Journal of Hypertension", Aug. 1994, 2(3), pp. 179-180; English abstract on p. 179.
Examiner's Report dated Dec. 7, 2023 issued in the corresponding Canadian Patent Application No. 3126331, total of 5 pages.
Decision on Rejection issued in Chinese Patent Application No. 202080008310.1, Jul. 30, 2024, with English translation (8 pages).
Yang Yajuan et al., The Second Military Medical University Press, May 2015, Edition 1, Print 1, p. 1, with English summary.
GT Mah et al: "Methyldopa for primary hypertension", Cochrane Database Syst Rev. 2009, 2009(4): CD003893. DOI: 10.1002/14651858. CD003893. pub3. (43 pages).
Examination Report dated Sep. 6, 2024 in the corresponding Australian Patent application No. 2020205863.
Examiner's Report dated Nov. 7, 2024 issued in the corresponding Canadian Patent Application No. 3126331 (3 pages).
Examination Report dated May 7, 2025 issued in the corresponding European Patent Application No. 20738052.8 (6 pages).

* cited by examiner

A.

Mean ± S.D., (n=4). **p<0.01 v.s. ctrl. ##p<0.01. v.s. BCAS

B.

Mean ± S.D., (n=4). **p<0.01 v.s. ctrl. ##p<0.01. v.s. BCAS

A.

Mean ± S.D., (n=8-10). *p<0.05 v.s. ctrl(control). #p<0.05 v.s.BCAS

B.

Mean ± S.D., (n=8-10). *p<0.05 v.s. ctrl(control). #p<0.05 v.s.BCAS

A.

B.

PHARMACEUTICAL COMPOSITION FOR TREATMENT OF DEMENTIA AND CEREBROVASCULAR DISORDERS

CROSS-REFERENCE TO RELATED APPLICATIONS

This application claims priority to and the benefit of U.S. Provisional Patent Application No. 62/790,305 filed Jan. 9, 2019, the entire contents of which are incorporated herein by reference.

TECHNICAL FIELD

The disclosures of the present application provide pharmaceuticals and methods for preventing or treating cerebrovascular disorders and dementia, or suppressing a progression of these diseases.

BACKGROUND ART

The cerebrovascular disorder encompasses in a broad sense both of a cerebral hemorrhage (that is, a hemorrhagic cerebrovascular disorder) and a cerebral infarction (that is, ischemic cerebrovascular disorder). Also according to the ICD-10 (International Classification of Diseases 10th edition by the World Health Organization), the dementia is defined as "syndromes which is usually caused by a chronic or progressive brain disease, which consists of dysfunctions in a large number of higher brain functions such as memory, thinking, faculty of orientation, understanding, calculation, learning, language, judgement and the others", and the higher brain dysfunction refers to an entire of cognitive dysfunction due to structural disorders in brain. Also the cognitive dysfunction encompasses mild cognitive dysfunctions which is a prodromal stage where they may progress to various kinds of dementias.

The vascular dementia (VaD) represents cerebrovascular disorders, for example, cognitive disorders which are due to cerebral hemorrhage or cerebral infarction. A disease prevalence of the vascular dementia is the next higher to that of Alzheimer's dementia, and is the highest among the early-onset dementia.

The inventors etc. of the present application have so far found an assay method or a screening method for detecting or evaluating a lipid peroxidation suppression using a fluorescent nitroxide probe compound, and also reported some candidate compounds showing a lipid peroxidation suppression activity when the screening method is conducted can show a therapeutic activity against age-related macular degeneration by an intraperitoneal administration of the compounds (see Patent document 1).

CITATION LIST

Patent Document

Patent Document 1: PCT International Patent Application No. PCT/JP2018/025496

SUMMARY OF INVENTION

Problems to be Solved by Invention

The disclosures of the present application provide pharmaceuticals and methods for preventing or treating cerebrovascular disorders (such as cerebral hemorrhage, and cerebral infarction), and/or dementia caused by these disorders (in particular, vascular dementia), or suppressing a progression of these diseases, by using certain compounds having antioxidative properties, in particular anti-lipid peroxidative properties.

Means to Solve Problems

The inventors found out that a pharmaceutical composition comprising certain compounds and pharmaceutically acceptable carriers is useful for preventing or treating cerebrovascular disorders and/or vascular dementia, or suppressing a progression of these diseases.

That is, the disclosures of the present application provide the following embodiments, but are not limited thereto.

[1] A pharmaceutical composition for preventing or treating a cerebrovascular disorder or a vascular dementia, or suppressing a progression of the diseases in a subject in need of treatment, the composition comprising one or more compounds selected from the following group, and a pharmaceutically acceptable carrier, a group consisting of apomorphine ((R)-(−)-apomorphine hydrochloride), eseroline ((−)-eseroline fumarate), ethoxyquin (6-ethoxy-2,2,4-trimethyl-1,2-dihydroquinoline), methyldopa (methyldopa sesquihydrate), olanzapine (2-methyl-4-(4-methyl-1-piperazinyl)-10H-thieno[2,3-b][1,5]benzodiazepine, methyl 3-amino-4-(phenylamino)benzoate, methyl 3-amino-4-((4-methoxyphenyl)amino)benzoate, methyl 3-amino-4-((3-methoxyphenyl)amino)benzoate, methyl 3-amino-4-(benzylamino)benzoate, methyl 3-amino-4-((1-phenylethyl)amino)benzoate, 1-(4-(trifluoromethoxy)phenyl)indolin-5-amine, 1-(3,5-dimethylphenyl)-1H-indol-6-amine, 1-(3,5-dimethylphenyl)indolin-6-amine, 1-(4-methoxyphenyl)-1H-indol-6-amine, 1-(4-(methylthio)phenyl)-1H-indol-6-amine, 1-(4-(trifluoromethoxy)phenyl)-1H-indol-5-amine, and indapamide (4-chloro-N-[(2RS)-2-methyl-2,3-dihydro-1H-indol-1-yl]-3-sulfamoyl benzamide).

[2] The pharmaceutical composition according to [1] wherein the compound is one or more compounds selected from the group consisting of ethoxyquin (6-ethoxy-2,2,4-trimethyl-1,2-dihydroquinoline), and methyldopa (methyldopa sesquihydrates).

[3] The pharmaceutical composition according to [1] which is used as an oral administration or an intraperitoneal administration.

[4] The pharmaceutical composition according to [1] wherein a subject in need of treatment is a mammalian.

[5] The pharmaceutical composition according to [1] wherein a subject in need of treatment is a human.

[6] The pharmaceutical composition according to [1] wherein a subject in need of treatment suffers from early-onset dementia.

[7] A method for preventing or treating cerebrovascular disorders or vascular dementia or suppressing a progression of the disease, which comprises administering a therapeutically effective amount of the compound described in [1] to a subject in need of treatment.

[8] Use of the compound described in [1] in a preparation of pharmaceuticals for preventing or treating a cerebrovascular disorder or a vascular dementia, or suppressing a progression of the disease.

[9] The compound described in [1] for use to prevent or treat a cerebrovascular disorder or a vascular dementia in a subject in need of treatment, or suppress a progression of the disease.

[10] A food or beverage for preventing or treating a cerebrovascular disorder or a vascular dementia, or suppressing a progression of the disease, the food or beverage comprising the compound described in [1].

[11] The food or beverage according to [10] which is a health food, a functional food, a food for specified health uses, a nutritional supplement, a food with a label of Reduction of Disease Risk Claims, or a food for the sick.

[12] A method for treating a disease due to a reduction of a myelin basic protein by matrix metalloproteinase 9 (MMP-9) or suppressing a progression of the disease, which comprises administering a therapeutically effective amount of the compound described in [1].

Effect of Invention

The pharmaceutical compositions comprising certain compounds having anti-lipid peroxidative property as disclosed herein are useful for preventing or treating cerebrovascular disorders or vascular dementia, or suppressing a progression of the diseases.

Figure 1:
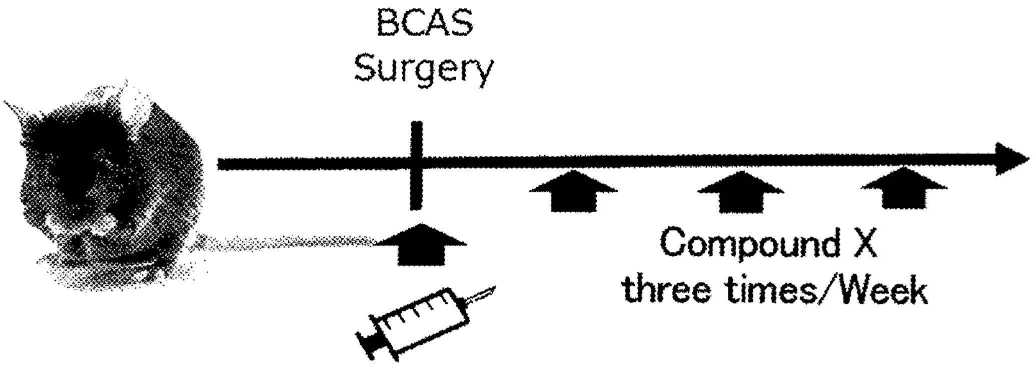
FIG. 1 is a drawing showing an administration of a compound to a mouse of vascular dementia disease model (Bilateral common artery stenosis (BCAS) model).

MODE FOR CARRYING OUT THE INVENTION (Pharmaceutical Use)

The "cerebrovascular disorder" represents collectively a disease caused by damaging a cerebral blood vessel. The cerebrovascular disorder is mainly divided into cerebral hemorrhage (hemorrhagic cerebrovascular disorder) and cerebral infarction (ischemic cerebrovascular disorder). The cerebrovascular disorder used herein encompasses both the cerebral hemorrhage and cerebral infarction, and the cerebral infarction is preferable. The cerebral hemorrhage is further divided into cerebral thrombosis and cerebral embolism depending on causes for clogging blood vessels. The cerebrovascular disorder used herein include one or more symptoms of these diseases or disorders.

The "dementia" is mainly divided into vascular dementia (VaD) and Alzheimer's dementia, however, the "dementia" disclosed herein represents a vascular dementia. The vascular dementia represents the cognitive disorder due to the above-mentioned cerebrovascular disorder, for example, the cerebral hemorrhage or cerebral infraction. The dementia disclosed herein encompasses core symptoms and peripheral symptoms which are occurred by accompanying with the core symptoms. Examples of the core symptoms may include any symptoms which have been known in the art, and for example, include cognitive dysfunctions such as memory impairment, executive function disorders, disorders of faculty of orientation, language disorder (aphasia), decrease in understanding and judgement, and apraxia and agnosia, which are not limited thereto. The peripheral symptoms represent a symptom which is more often appeared as the dementia progresses from a moderate degree thereof to a severe degree thereof. Examples of the peripheral symptoms include delusion, sleep disorder, depression, illusion, aggressive behavior or excitement, decreased motivation, wandering, resistance to long-term care, fall due to hyperactivity, and disorders of swallowing such as suffocation due to impulsive stealthy eating and so on, and are not limited thereto.

The "vascular dementia" used herein encompasses early-onset dementia to which is collectively referred by including a juvenile dementia which is occurred from eighteen (18) ages to thirty-nine (39) ages, in addition to a presenile dementia which is occurred from forty (40) ages to sixty-four (64) ages which have been hereto advocated.

The "myelin basic protein" represents a characteristic major protein which is localized in myelin (myelin sheath), and oligodendroglia cell (in central nervous tissue) or Schwann cell (in peripheral nerve tissue) which is a myelinating cell. A matrix metalloproteinase 9 (MMP-9) is known to be involved in a destruction of blood-brain barrier (see for example, Barr, T L et al., Stroke, 2010, 41, e123-e128), and a decomposition of myelin basic protein is observed due to some factors such as matrix metalloproteinase-9 (MMP-9). Accordingly, the protein is useful as an index investigating diagnosis, treatment, prevention or suppression of the cerebrovascular disorders or vascular dementia.

As used herein, the "treatment or treating" or "prevention or preventing" or "suppression or suppressing of a progression" against cerebrovascular disorder and/or vascular dementia encompasses at least one of the followings. (1) excluding the above-mentioned cerebrovascular disorder and/or vascular dementia, for example, one or more of the above-mentioned specific diseases, typically the vascular dementia, and one or more of the relevant symptoms; (2) reducing or minimizing the degree of seriousness of the above-mentioned cerebrovascular disorder and/or the vascular dementia, for example, one or more of the above-mentioned specific diseases, typically the vascular dementia and one or more of the relevant symptoms: (3) delaying the progression or the onset of the above-mentioned cerebrovascular disorders and/or the vascular dementia, for example, one or more of the above-mentioned specific diseases, typically, the vascular dementia and one or more of the relevant symptoms; and (4) lowering, minimizing or excluding an incidence or a frequency of the above-mentioned cerebrovascular disorders and/or the vascular dementia, for example, one or more of the above-mentioned specific diseases, typically, the vascular dementia and one or more of the relevant symptoms.

The "subject" in need of the treatment and so on used herein represents mammalian, and includes human or non-human animals, and preferably include human. The subject encompasses person of advanced ages of 60 ages or more (such as 65 ages or more, or 70 ages or more), the above-mentioned younger people from 18 ages or more to less than 40 ages; and the above-mentioned presenile people from 40 ages or more to less than 60 ages. The subject as a target for the treatment by the present invention used herein encompasses the subjects having one or more of the diseases or disorders of the cerebrovascular disorders and/or the vascular dementia, or one or more of the relevant symptoms.

The present invention provides a pharmaceutical composition as an oral administration use or an intraperitoneal administration use for preventing or treating cerebrovascular disorders and/or vascular dementia, or suppressing a progression of the diseases in a subject in need of the treatment and so on, the composition comprising as an active drug a therapeutically effective amount of one or more of the compounds selected from the following group (hereinafter, the compound may be referred to as “active drug of the present invention”, or “present compound”) and a pharmaceutically acceptable carrier (hereinafter, the pharmaceutical composition may be referred to as “pharmaceutical composition of the present invention” or “present pharmaceutical composition”). Examples of the active drug include the following groups: a group consisting of apomorphine ((R)-(−)-apomorphine hydrochloride), eseroline ((−)-eseroline fumarate), ethoxyquin (6-ethoxy-2,2,4-trimethyl-1,2-dihydroquinoline), methyldopa (methyldopa sesquihydrate), olanzapine (2-methyl-4-(4-methyl-1-piperazinyl)-10H-thieno[2,3-b][1,5]benzodiazepine, methyl 3-amino-4-(phenylamino)benzoate, methyl 3-amino-4-((4-methoxyphenyl)amino)benzoate, methyl 3-amino-4-((3-methoxyphenyl)amino)benzoate, methyl 3-amino-4-(benzylamino)benzoate, methyl 3-amino-4-((1-phenylethyl)amino)benzoate, 1-(4-(trifluoromethoxy)phenyl)indolin-5-amine, 1-(3,5-dimethylphenyl)-1H-indol-6-amine, 1-(3,5-dimethylphenyl)indolin-6-amine, 1-(4-methoxyphenyl)-1H-indol-6-amine, 1-(4-(methylthio)phenyl)-1H-indol-6-amine, 1-(4-(trifluoromethoxy)phenyl)-1H-indol-5-amine, and indapamide (4-chloro-N-[(2RS)-2-methyl-2,3-dihydro-1H-indol-1-yl]-3-sulfamoyl benzamide).

Here, the compounds which are included in the above-mentioned compound group are compounds which are found to show any permeability of the blood-brain barrier, and also a lipid peroxidation suppression effect in PCT/JP 2018/025496 filed by the inventors and so on of the present application. The structural formulae of these compounds are indicated below.

Apomorphine: ((R)-(−)-Apomorphine hydrochloride):

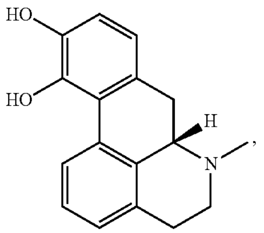

Eseroline: ((−)-Eseroline fumarate):

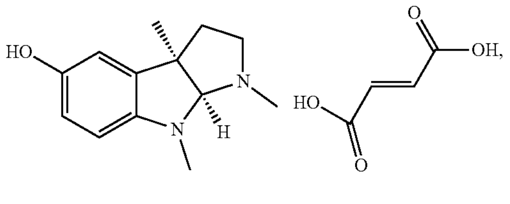

Ethoxyquin: (6-Ethoxy-2,2,4-trimethyl-1,2-dihydroquinoline):

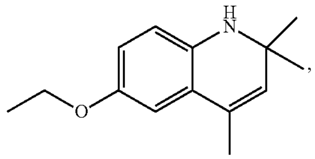 [SMILES: CCOc1ccc2c(c1)C(C)=CC(C)(C)N2]

Methyldopa: (Methyldopa sesquihydrates):

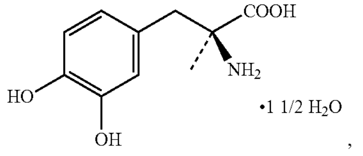

Olanzapine: (2-Methyl-4-(4-methyl-1-piperazinyl)-10H-thieno[2,3-b][1,5]benzodiazepine):

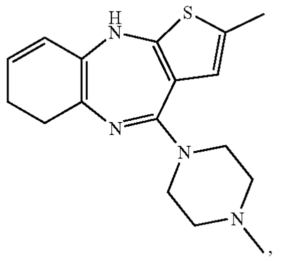 [SMILES: Cc1cc2c(s1)NC1=C(CCC=C1)N=C2N1CCN(C)CC1]

Methyl 3-amino-4-(phenylamino)benzoate:

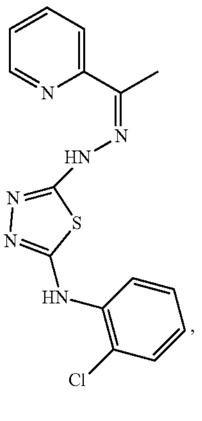 [SMILES: C/C(=N/Nc1nnc(Nc2ccccc2Cl)s1)c1ccccn1]

Methyl 3-amino-4-(benzylamino)benzoate:
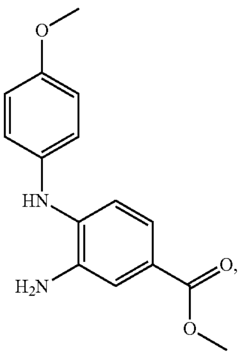 [SMILES: COC(=O)c1ccc(Nc2ccc(OC)cc2)c(N)c1]
Methyl 3-amino-4-((1-phenylethyl)amino)benzoate:
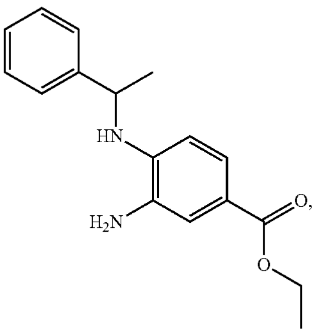 [SMILES: CCOC(=O)c1ccc(NC(C)c2ccccc2)c(N)c1]
1-(4-(Trifluoromethoxy)phenyl)-1H-indol-5-amine:
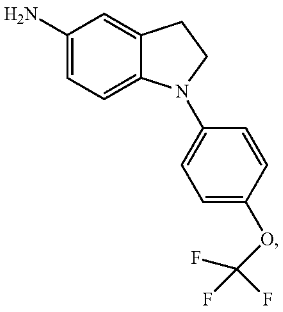 [SMILES: Nc1ccc2c(c1)CCN2c1ccc(OC(F)(F)F)cc1]
1-(3,5-Dimethylphenyl)-1H-indol-6-amine:
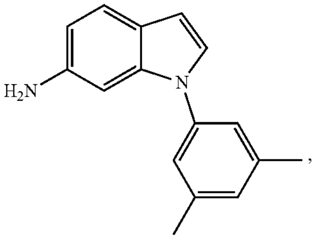 [SMILES: Cc1cc(C)cc(-n2ccc3ccc(N)cc32)c1]
1-(3,5-Dimethylphenyl)indolin-6-amine:
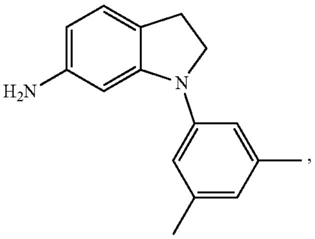
1-(4-Methoxyphenyl)-1H-indol-6-amine:
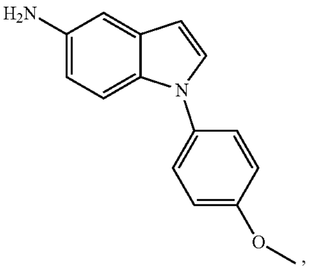 [SMILES: CSc1ccc(-n2ccc3cc(N)ccc32)cc1]
1-(4-(Methylthio)phenyl)-1H-indol-6-amine:
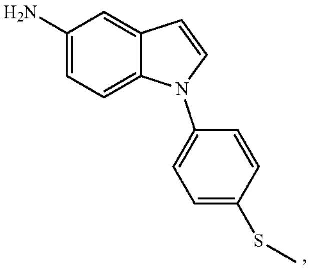
1-(4-(Trifluoromethoxy)phenyl)-1H-indol-5-amine:
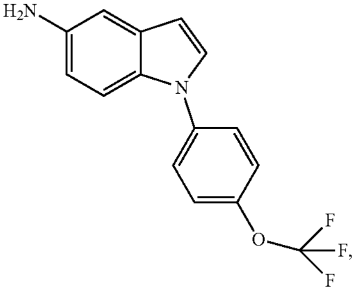 [SMILES: Nc1ccc2c(ccn2-c2ccc(OC(F)(F)F)cc2)c1]

Indapamide: (4-Chloro-N-[(2RS)-2-methyl-2,3-dihydro-1H-indol-1-yl]-3-sulfamoyl benzamide):

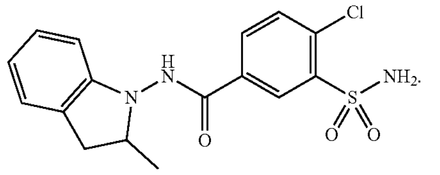 [SMILES: CC1Cc2ccccc2N1NC(=O)c1ccc(Cl)c(S(N)(=O)=O)c1]

The present compound as active drug includes the forms of the above-mentioned compounds and pharmaceutically acceptable salts thereof. Also, the active drug of the present invention or a pharmaceutically acceptable salt thereof includes a hydrate or a solvate thereof with a solvent or the like. The present invention further includes any form of crystal of the active drug of the present invention.

Examples of the pharmaceutically acceptable salts include salts with organic bases (for example, diethanolamine salts, ethylenediamine salts), and salts with inorganic bases (for example, salts with alkali metals (for example, sodium, or potassium) and salts with alkaline earth metals (for example, calcium, or magnesium).

According to one embodiment, the compound as active drug is preferably one or more compounds selected from the following group: a group consisting of apomorphine ((R)-(−)-apomorphine hydrochloride), eseroline ((−)-eseroline fumarate), ethoxyquin (6-ethoxy-2,2,4-trimethyl-1,2-dihydroquinoline), methyldopa (methyldopa sesquihydrate), olanzapine (2-methyl-4-(4-methyl-1-piperazinyl)-10H-thieno[2,3-b][1,5]benzodiazepine, and indapamide (4-chloro-N-[(2RS)-2-methyl-2,3-dihydro-1H-indol-1-yl]-3-sulfamoyl benzamide).

According to one embodiment, the compound as active drug is more preferably one or more compounds selected from the following group: a group consisting of ethoxyquin (6-ethoxy-2,2,4-trimethyl-1,2-dihydroquinoline), and methyldopa (methyldopa sesquihydrates).

As used herein, an "effective amount" represents an amount of an active drug which is sufficient to provide the desirable effect, that is, the treatment or prevention of the cerebrovascular disorders or the vascular dementia, or the suppression of the progress of the diseases, which are as described herein. Also the active drug or the pharmaceutical composition of the present invention may be used in combination with a publicly known active drug or a pharmaceutical composition for the intended diseases or the relevant symptoms.

According to one embodiment, the effective amount used herein may be any dose as long as it is the dose capable of preventing an onset of the cerebrovascular disorders or the vascular dementia, treating the symptoms of the diseases, or suppressing (improving) the progress of the symptoms of the disease when the present compound as active drug is administered. In the case of an oral administration, the dose may be an orally therapeutically effective amount, and in the case of an intraperitoneal administration, the dose may be an intraperitoneally effective amount.

The dose range of the effective amount can be adjusted appropriately depending on a condition including a selection of the compound used, an administration route (for example, an oral administration or an intraperitoneal administration), a property of a drug formulation, a type, age, weight or sex of a subject, or a property of a symptom or a degree of seriousness.

The effective amount of the present compound is about 80% by weight or less, and more preferably about 50% by weight or less based on the weight of the pharmaceutical composition for oral administration or the pharmaceutical composition for intraperitoneal administration, and is not limited thereto.

Examples of the effective amount of the present compound include about 0.001 to about 50 mg/weight kg per a daily dosage. For example, in the case of the oral administration or the intraperitoneal administration, the daily dosage is about 0.1 to about 50 mg/kg, usually about 0.2 to about 10 mg/kg, preferably about 0.3 to about 2 mg/kg, and more preferably about 0.4 to about 1 mg/kg, which is not limited thereto.

The present compound or the pharmaceutical composition of the present invention can be administered once per day, or a plural times per day (for example, in the case of the oral administration or the intraperitoneal administration, they can be administered in two or three divided times per day). Also they can be administered once or a plural times within several days or several weeks.

As used herein, the term of "administer (or administration)" represents that the present compound or the pharmaceutical composition of the present invention is provided or prescribed to an individual of subject, or the individual receives the present compound or the pharmaceutical composition of the present invention; and so on. The administration route of the present compound or the pharmaceutical composition may be either an oral administration route or an intraperitoneal administration route, which can vary depending on intended disease or symptom, or age, weight or sex of the subject, or the like, and is preferably the oral administration in terms of an easy of administration and a lowering of dose and so on.

The pharmaceutical composition of the present invention can be administered by an oral administration route or an intraperitoneal administration route to the subject.

The pharmaceutical composition of the present invention can be prepared as the pharmaceutical composition for oral administration or the pharmaceutical composition for intraperitoneal administration by using conventionally publicly known technologies, and thereby can contain a non-toxic and inert carrier or additive (hereinafter, referred to as "pharmaceutically acceptable carrier") which is usually used in the pharmaceutical field. For example, the pharmaceutical composition for oral administration (oral formulations) is formulated into, for example, tablets, fine granules, capsules, pills, granules, powders, solutions, and suspensions and so on, which is not limited thereto. Also the pharmaceutical composition for intraperitoneal administration may be formulated into a dosage form such as injectables and so on.

The "pharmaceutically acceptable carrier" used herein may be contained by combining various active ingredients or medicinal ingredients (including pharmacological active ingredients or physiologically active ingredients) or additives (for example, excipients, lubricants, binders, disintegrants, emulsifier, stabilizer, correctives, diluents, tonicity agents, buffer agents, pH adjusting agents, solubilizers, thickening agents, dispersing agents, preservatives (antiseptics)) in addition to the present compound as active drug depending on various kinds of usages such as the administration route and the dosage form as long as a pharmacological effect is not disturbed. These ingredients may be compounded appropriately within certain concentration ranges which do not affect any irritation and so on, and the kinds of the ingredients are not particularly limited thereto.

When the present compound or the pharmaceutical composition of the present invention is used as the pharmaceutical composition for oral administration, pharmaceutically acceptable carriers such as excipients, lubricants, binders, disintegrants, emulsifying agent, stabilizer, correctives, or diluents may be contained.

Examples of the excipients include organic excipients and inorganic excipients. Examples of organic excipients include one or more compounds selected from sugar derivatives (such as lactose, sucrose, glucose, mannitol, and sorbitol), and starch derivatives (such as corn starch, potato starch, α-starch, and dextrin), cellulose derivatives (such as crystalline cellulose), gum arabic, dextran, prolan and the others. Examples of the inorganic excipients include one or more compounds selected from light anhydrous silicic acid and sulfates (such as calcium sulfate).

Examples of the lubricants include one or more compounds selected from stearic acid, metal stearates (such as calcium stearate and magnesium stearate), talc, colloidal silica, waxes (such as bead wax), adipic acid, sulfates (such as sodium sulfate), glycol, fumaric acid, sodium benzoic acid, D,L-leucine, sodium lauryl sulfate, silic acids (such as silicic acid anhydride, silicic acid hydrate), and starch derivatives described as the above-mentioned excipients.

Examples of the binders include one or more compounds selected from hydroxypropyl cellulose, hydroxypropylmethyl cellulose, polyvinylpyrrolidone, macrogol, and compounds described as the above-mentioned excipients.

Examples of the disintegrants include one or more compounds selected from cellulose derivatives (such as low substituted hydroxypropyl cellulose, carboxymethyl cellulose, calcium carboxymethyl cellulose, and internally crosslinked carboxymethyl cellulose calcium), and chemically modified starch and cellulose derivatives (such as carboxymethyl starch, and carboxymethyl starch sodium).

Examples of the emulsifying agents include one or more compounds selected from colloidal clay (such as bentonite, and Veegum), anionic surfactants (such as sodium lauryl sulfate), cationic surfactants (such as benzalkonium chloride), and nonionic surfactants (such as polyoxyethylene alkyl ether, polyoxyethylene sorbitan fatty acid ester, and sucrose fatty acid ester).

Examples of the starbilizer include one or more compounds selected from p-hydroxy benzoic esters (such as methyl paraben, and propyl paraben), alcohols (such as chlorobutanol, benzyl alcohol, and phenylethyl alcohol), phenols (such as phenol, and cresol), thimerosal, acetic anhydride, and sorbic acid.

Examples of the correctives include one or more compounds selected from sweetness (such as saccharin sodium, and aspartame), acidulants (such as citric acid, malic acid, and tartaric acid), and fragrances (such as menthol, and fruit extracts (such as orange extract)).

Examples of the diluents include one or more compounds selected from lactose, mannitol, glucose, sucrose, calcium sulfate, hydroxypropyl cellulose, microcrystalline cellulose, water, ethanol, polyethylene glycol, propylene glycol, glycerol, starch, and polyvinylpyrrolidone.

When the present compound or the pharmaceutical composition of the present invention is used as the pharmaceutical composition for intraperitoneal administration, the composition may contain any carriers which may be in general compounded for injectable. Examples of the carriers include pharmaceutically acceptable carriers such as solvents, dissolving aids, preservatives, stabilizers, emulsifying agents and suspending agents, tonicity agent and buffer agents, pH adjusting agents, excipients, and colorants.

Examples of the solubilizers may include either aqueous solubilizers or nonaqueous solubilizers, and preferably aqueous solubilizers. Examples of the aqueous solubilizers include aqueous solution, and specifically include one or more compounds selected from distilled water for injection which is stipulated in the pharmacopoeia, normal saline solution, and Ringer's solution. Examples of the nonaqueous solubilizers include pharmaceutically acceptable vegetable oils (such as purified peanuts oils, sesame oils, corn oils, olive oils, and cottonseed oils), and are not limited thereto.

Examples of the dissolving aids include one or more compounds selected from sodium benzoic acid derivatives (such as sodium benzoate of caffeine), aminophylline derivatives (such as ethylenediamine of aminophylline), and meglumine derivatives (such as adipione meglumine).

Examples of the preservatives include one or more compounds selected from benzalkonium chloride, benzethonium chloride, benzyl alcohol, chlorobutanol, methyl paraoxybenzoate, and phenol.

Examples of the stabilizer may be the same as those used in the pharmaceutical composition for oral administration, and include, for example, one or more compounds selected from nitrite salts, sodium metabisulfite, ascorbic acid, as needed sodium edetate (EDTA), and thioglycolic acid.

Examples of the emulsifying agent or suspending agent may be the same as those used in the pharmaceutical composition for oral administration, and include, for example, one or more compounds selected from nonionic surfactants, lecithin and pluronic.

Examples of the tonicity agents include one or more compounds selected from glycerin, propylene glycol, sodium chloride, calcium chloride, sorbitol, and mannitol.

Examples of the buffer agents include one or more compounds selected from phosphoric acid, phosphate salt, citric acid, acetic acid, and ε-amino caproic acid.

Examples of the pH adjusting agents include one or more compounds selected from hydrochloric acid, citric acid, phosphoric acid, acetic acid, sodium hydroxide, calcium hydroxide, boric acid, borax, sodium hydrogen phosphate, sodium dihydrogen phosphate, sodium carbonate, and sodium hydrogen carbonate.

Examples of the excipients include sorbitol and the like.

Examples of the colorants include pharmaceutically acceptable additives.

The pharmaceutical composition of the present invention, the agent for oral administration of the present invention, or the agent for intraperitoneal administration of the present invention may further contain one or more compounds for increasing efficacies. Examples of such a compound may include antibiotics, steroids, anti-inflammatory agents, analgesic agents, surfactants, chelating agents, and adjuvants, and any combinations of two or more of them, but are not limited thereto.

In the food or beverage of the present invention, the food or beverage may be compounded by the active ingredient of the present invention as itself, or in the form of a composition comprising the same active ingredient that is mixed with other additives as needed. For example, the food or the beverage of the present invention may be a product prepared by adding with conventional additive ingredients such as stabilizers to the active ingredient of the present invention followed by formulating into a food or a beverage, a product prepared by compounding various kinds of proteins, sugars, fats, trace elements, vitamins, and so on into the above produced food or beverage followed by formulating into a food or a beverage, a food or beverage produced by formulating into a form of liquid, semi-liquid or solid, or a food or a beverage produced by formulating into a form of a paste, or a food or a beverage produced by adding active ingredient into a generally used food or beverage followed by formulating into a food or beverage.

In the present invention, the "food or a beverage" may be anything other than pharmaceuticals, and is not particularly limited as long as it is in the form being capable of oral intake by mammals, and the form may be any ones such as liquids (such as solutions, suspensions, and emulsions), semi-liquids, powders, or solid molded products. Accordingly, the food or the beverage may be, for example, in form of beverage, or in form of tablet of a nutritional supplement such as so-called a supplement.

Specific examples of the food or the beverage include instant foods such as instant noodles, Retortable foods, canning foods, microwave foods, instant soups, miso soups, and freeze-dried foods; beverages such as refreshing beverages, fruit juice beverages, vegetable juice beverages, soy milks, coffee beverages, tea beverages, powdered beverages, concentrated beverages, nutritional beverages, and alcoholic beverages; flour products such as breads, pastas, noodles, cake mixes, fried chicken powders, and breadcrumbs; confectioneries such as candy, caramel, chewing gum, chocolate, cookies, biscuits, cake, pie, snacks, cracker, Japanese sweets, and desserts sweet; seasonings such as sauces, tomato processed seasonings, flavor seasonings, cooking mix, drippings, dressings, soups, and bases for curry and stew; oils and fats such as modified fats, butter, margarine, and mayonnaise; dairy products such as milk based beverage, yogurts, lactic fermenting beverage, ice creams, and creams; processed marine products such as fish meat ham and sausage, and seafood-pastes; processed animals products such as livestock meat ham and sausage; agricultural processed products such as canned agricultural products, jams, and marmalades, pickles, boiled beans, and cereal; frozen foods; and nutritional foods, and the like.

The food or the beverage of the present invention can be used preferably a subject who is disposed to a prevention or treatment of the above-mentioned cerebrovascular disorders or dementia, or a suppression of a progress on the diseases.

In the present invention, the "food or beverage" may encompass such a classification as health food, functional food, food for specified health uses, nutritional supplement, foods a label of Reduction of Disease Risk Claims, or food for the sick. Further, the "food or beverage" may be used to encompass feeds when it is applied to mammalians other than human as a target. As used herein, the "food for specified health uses" represents a food in which any legal limitations are subjected in each country (such as Japan) from the viewpoint of health in the case where such action as a preparation or sales of a food is conducted for the purpose of an expression of a desirable effect. Such a food may be a food with a label indicating that the food has a possibility of reducing a disease risk, that is, a food with a label of Reduction of Disease Risk Claims. Here the "Reduction of Disease Risk Claims" may be an indication representing a food having a possibility of reducing a disease risk and also representing a prescribed indication or an authorized indication on the basis of a standard set by FAO/WHO Codex Alimentarius Commission itself or as a reference.

In the food or beverage of the present invention, any ingredients having the other function(s) may be further added in addition to the above-mentioned active ingredients. Also for example, the active ingredients of the present invention is compounded to foods to be ingested in daily life, health food, functional food, supplement (for example, a food containing one or more kinds of ingredients selected from minerals such as calcium and magnesium or vitamins (such as vitamin K)), and thereby any food or beverage having any function due to the other ingredient together with the effect of the present invention can be provided.

In the preparation of the food or beverage of the present invention, sugars, fragrances, fruit juice extracts, food additives, or stabilizer which are used in a usual prescription design of food or beverage can be added appropriately. The preparation of the food or beverage can be conducted by referring to preparation technologies which are publicly known in the technical fields. The food or beverage of the present invention can take various kinds of forms thereof, and the food or beverage of the present invention may be prepared according to a similar technology to the preparation technologies of publicly known pharmaceutical products. In these cases, the food or beverage of the present invention can be prepared by using the carrier or additives as described in the items of preparation of the agent or the pharmaceuticals of the present invention. Also in the preparation stage, the food or beverage of the present invention may be combined with other ingredients which exert any functions other than the functions of the present invention or other functional foods to make a food or beverage having multifunctions.

In the embodiments as disclosed herein, when ethoxyquin or methyldopa is administered as an active ingredient to a mouse as vascular dementia disease model by an oral administration or an intraperitoneal administration, the results of a suppression of blood-brain barrier disruption, an inhibition of a reduction in myelin basic protein, and an influence on cerebral blood flow are examined, and as a result thereof, it was suggested that some activities on treatment for vascular dementia and the like are exhibited.

EXAMPLES

The present invention is more specifically explained by the Formulation Examples and Test Examples as follows, and the present invention is not limited to these examples. The compounds, the mice, and the reagents which are used in the Examples were available from commercial sources or prepared according to publicly known methods.

Formulation Examples

The Formulation examples of the pharmaceutical composition of the present invention are shown below, and are not limited thereto.

Formulation Example 1

Tablet

TABLE 1

| In 100 mg | |
|---|---|
| Methyldopa | 25 mg |
| Lactose | 49.5 mg |
| Corn starch | 11 mg |
| Carboxymethyl cellulose calcium | 7 mg |
| Hydroxypropyl cellulose | 7 mg |
| Magnesium stearate | 0.5 mg |

A tablet is prepared by a generally known formulating method of a tablet. Specifically, methyldopa as the present compound, corn starch, and lactose are mixed in a mixer, and carboxymethyl cellulose calcium, and hydroxypropyl cellulose are added to the mixture, and the mixture is granulated, and the resulting granules are subjected to a grain size procedure after drying, and magnesium stearate is added to the granules with grained size, and mixed with each other, and the mixture is compressed with a tableting machine. Also by changing an addition amount of the present compound, certain tablets containing a desirable amount of the present compound (such as 10 mg, 25 mg, or 50 mg) in a 100 mg tablet can be prepared.

Test Example

A test wherein an efficacy of the present compound on a treatment for cerebrovascular disorders or vascular dementia is examined is described.

Test Example 1

Preparation of Vascular Dementia Disease Model Mouse

Firstly, according to a general preparation method for vascular dementia disease model mouse (for example, Shibata M, Ohtani R, Ihara M, et al., Stroke 35: 2598-2603, 2004; or Ihara M, Taguchi A, Maki T, et al., Methods Mol Biol 1135: 95-102, 2014), the mouse was equipped with a 0.18 mm microcoil into a right common carotid artery of the mice and a 0.16 mm microcoil into a left common carotid artery thereof.

Next, a vascular dementia disease model mouse (hereinafter sometimes referred to as Bilateral common artery stenosis (BCAS) model) was prepared according to the below-mentioned schedule as shown in FIG. 1.

Ethoxyquin or methyldopa were administered by an oral administration or an intraperitoneal administration in a dose of 100 μmol/kg by a ratio of three times/week until the completion of the test (for example, for 1 to 4 weeks). Here the test results in the case where a healthy mouse as control was used is shown.

Test Example 2

Test for Suppression of Blood-Brain Barrier Disruption

The vascular dementia disease model mouse which was prepared in the Test Example 1 was euthanized on 7 days after the surgery. The hippocampus and striatal tissue of the mice (N (number of animal)) were placed in a 20 times volume of lysis buffer containing benzyl sulfonyl fluoride, protease inhibitor cocktail and sodium orthovanadate to make a homogenate. The homogenate was crushed with ultrasonic while cooling on ice, and after centrifuging, the supernatant was subjected to a protein quantification by a bicinchoninic acid (BCA) method. Thereafter, the prepared protein sample was evaluated on an effect on suppression of blood-brain barrier disruption according to a western blotting method using antibody against matrix metalloproteinase 9 (MMP-9) similarly to a generally known method.

Mean+S.D., (n=4), **p<0.01 v.s. ctrl, ##p<0.01, v.s. BCAS

Figure 2:
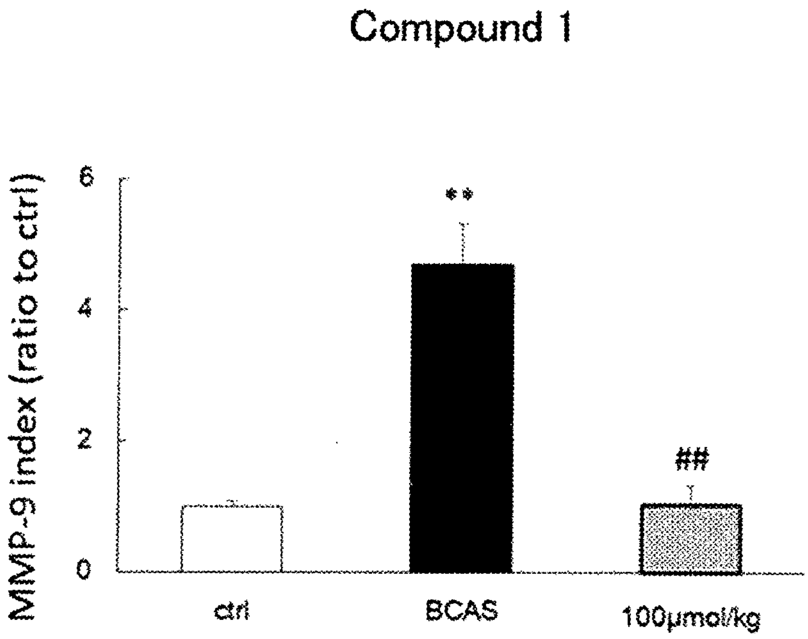
FIG. 2 is a drawing showing a test result on suppressing a blood-brain barrier disruption. It shows a test result (A) obtained when ethoxyquin (Compound 1) was administered, and a test result (B) obtained when methyldopa (Compound 2) was administered.
Figure 2:
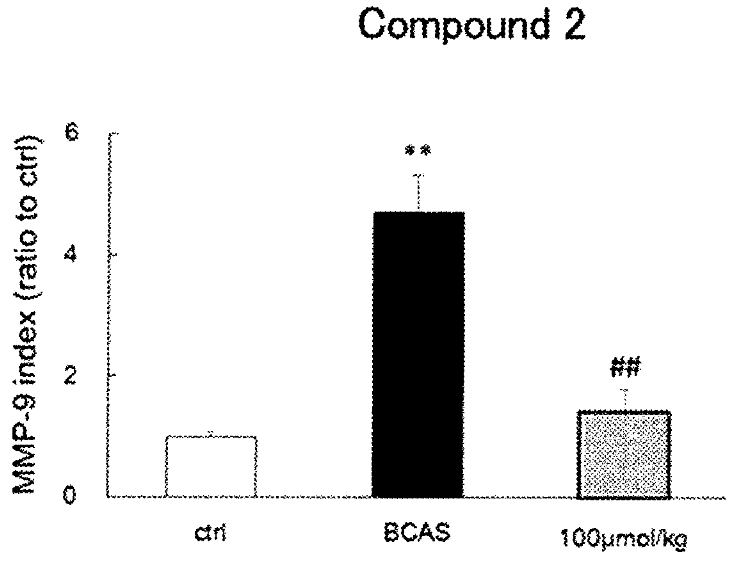

The test results are shown in FIG. 2. Compound 1 (ethoxyquin) (A) and the compound 2 (methyldopa) (B) suggested an effect on suppressing a blood-brain barrier disruption.

Test Example 3

Test for Suppression Against Reduction of a Myelin Basic Protein (MBP)

The vascular dementia disease model mouse which was prepared in the Test Example 1 was euthanized on 28 days after the surgery. The frozen section of the brain of the mice (N (number of animal)=6 to 8 animals) were immobilized in cold acetone for 10 minutes, and washed with PBS for 5 minutes (× three times). An endogenous peroxidase was subjected to a blocking with 0.3% hydrogen peroxide solution for 10 minutes, and was then allowed to a reaction with anti-MBP polyclonal antibody for a day. Thereafter, the endogenous peroxidase was washed with PBS for 5 minutes (× three times) and was reacted with the secondary antibody for 60 minutes. Thereafter, the sample was mounted by using a prolong gold antifade mountant for cell fixation containing 4',6-diamidino-2-phenylindole (DPI) (ProLong (registered trademark) Gold antifade reagent with DAPI) (manufactured by Invitrogen), and was observed and imaged by a confocal laser scanning biological microscope (such as LSM 700).

Figure 3:
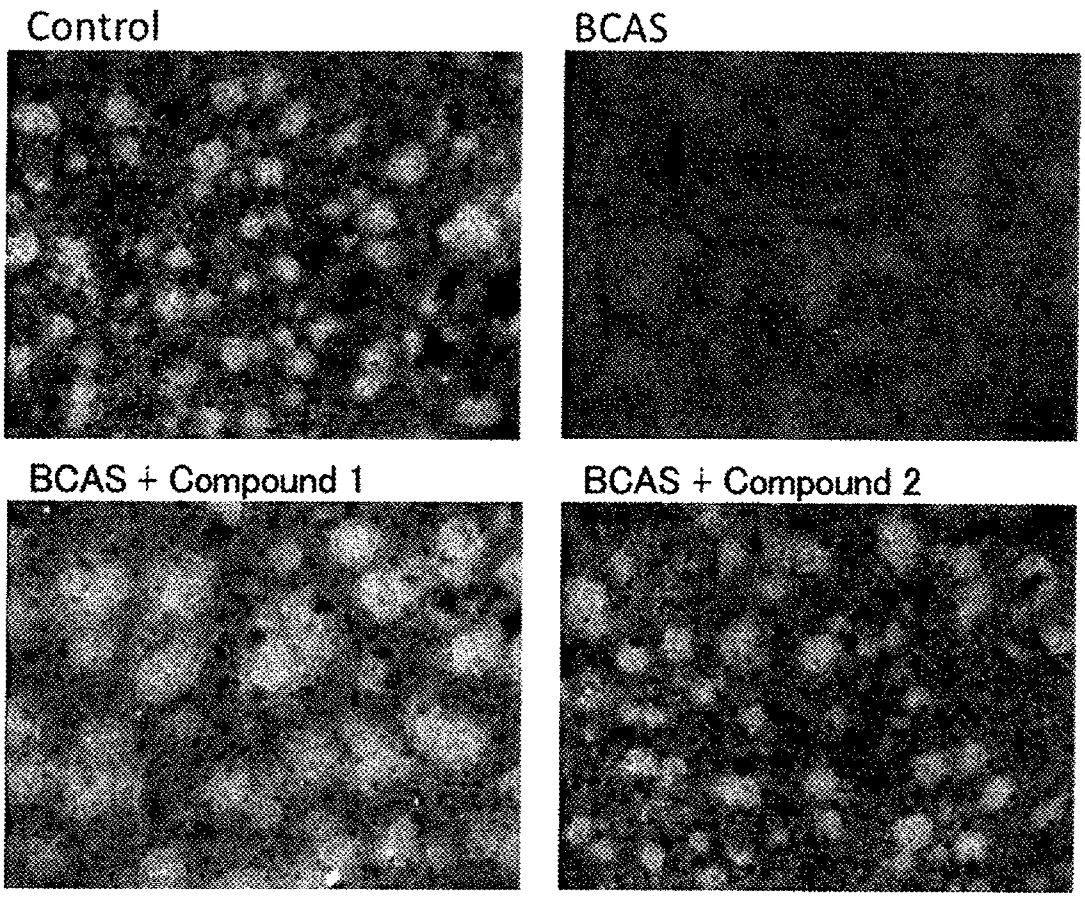
FIG. 3 is a drawing showing a test result on suppressing the reduction of a myelin basic protein.

The test results are shown in FIG. 3. The compound 1 (ethoxyquin) and the compound 2 (methyldopa) were suggested an effect on a suppression of the reduction of myelin basic protein.

Test Example 4

Novel Object Recognition Test

A novel object recognition test was conducted by utilizing rodent's character of seeking novelty. The vascular dementia disease model mouse (N (number of animal)=8 to 10 animals) that was prepared in the test example 1 was accustomed in advance to an observation box, and they were placed in the same observation box after two hours, and the two of the same objects were explored freely for 10 minutes (Acquisition trial). After a certain times were passed, one of the object was changed by a novel object, and the animals were placed in the same observation box again, and the time exploring an object was measured for 10 minutes (Test trial). The time exploring a novel object or the time exploring the learned object were defined as "N" or "F" respectively, and were calculated by the following equation: the Exploration time=N+F, and the Discrimination Index=(N−F)/(N+F).

Mean+S.D., (n=8-10), *p<0.05 v.s. ctrl(control), #p<0.05 v.s. BCAS

Figure 4:
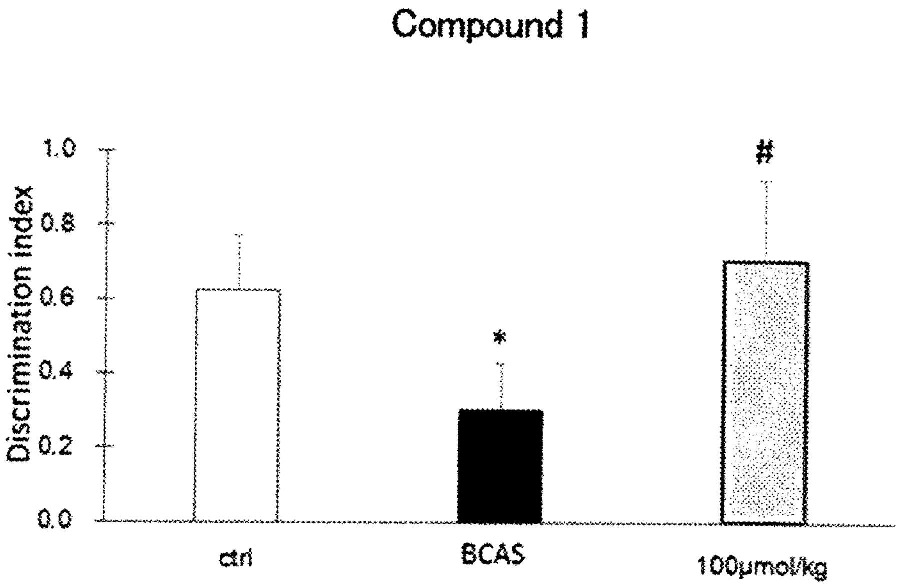
FIG. 4 is a drawing showing a novel object recognition. It indicates a test result (A) obtained when ethoxyquin (Compound 1) was administered, and a test result (B) obtained when methyldopa (Compound 2) was administered.
Figure 4:
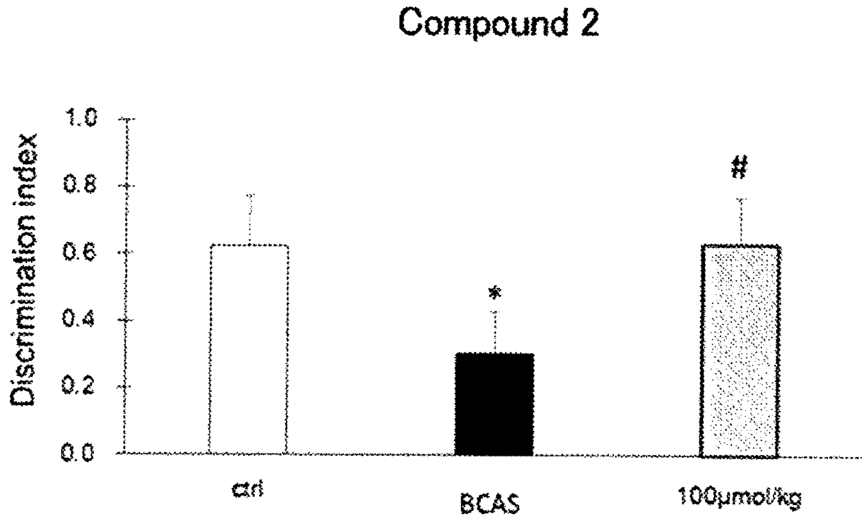

The test results are shown in FIG. 4. The compound 1 (ethoxyquin) (A) and the compound 2 (methyldopa) (B) showed an improved cognitive dysfunction in a long-term spatial memory.

Test Example 5

Test for Influence on Cerebral Blood Flow

In the vascular dementia disease model mice (N (number of animals)=6 to 8 animals) that were prepared in the Test Example 1, a cerebral blood flow of a boundary region (blegma) between middle cerebral artery and anterior cerebral artery was measured at immediately before ischemic surgery, immediately after ischemic surgery, after 1 day, after 4 days, after 7 days or after 14 days. A Laser-Doppler blood flow meter was fixed on a skull, and a cerebral blood flow was measured, and the cerebral blood flow was evaluated as a ratio thereof to cerebral blood flow immediately before ischemic surgery.

Ethoxyquin or methyldopa were administered by an oral administration or an intraperitoneal administration in a dose of 50, 75 or 100 μmol/kg by a ratio of three times/week until the completion of the test (for example, for 1 to 4 weeks).

Figure 5:
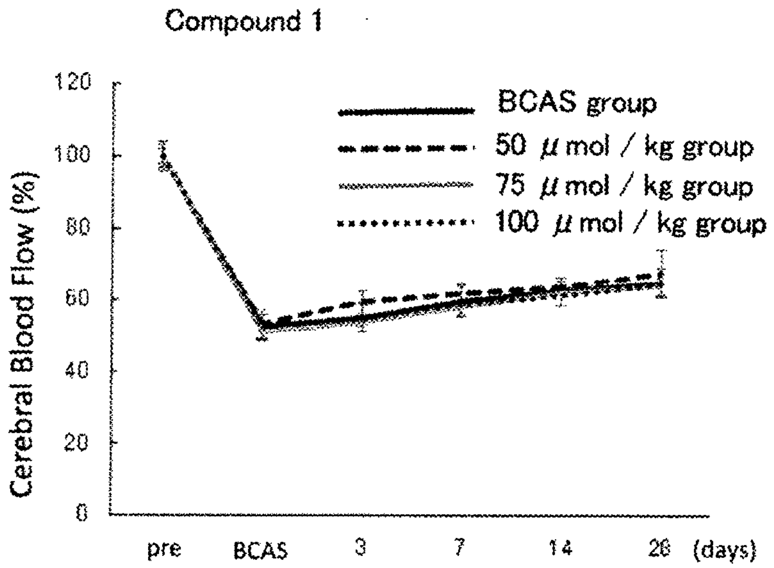
FIG. 5 is a drawing showing a test result on a cerebral blood volume. It indicates a test result obtained when ethoxyquin (Compound 1) is administered, and a test result obtained when methyldopa (Compound 2) was administered.
Figure 5:
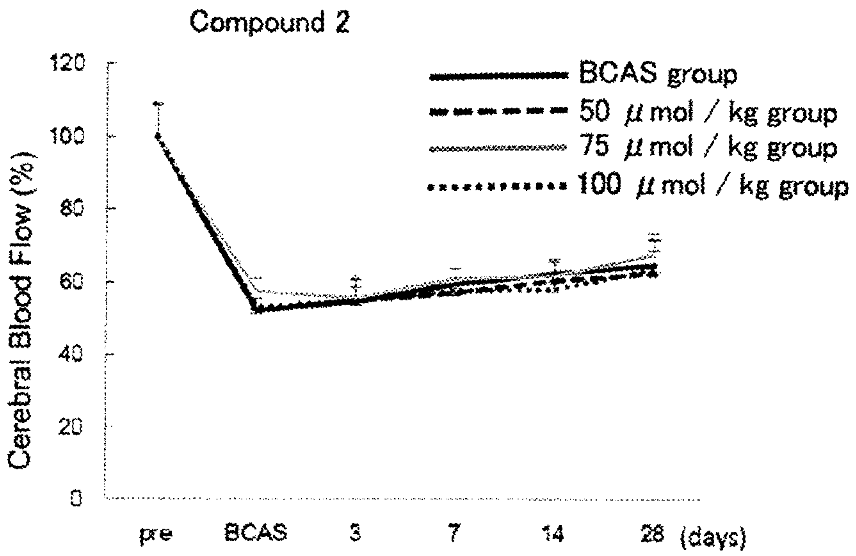

The test results are shown in FIG. 5. It was suggested that the compound 1 (ethoxyquin) (A) and the compound 2 (methyldopa) (B) do not affect any cerebral blood flow.

INDUSTRIAL APPLICABILITY

The present compound or the pharmaceutical composition of the present invention is useful as pharmaceuticals for an oral administration or an intraperitoneal administration for treatment and the like of cerebrovascular disorders or vascular dementia.

The invention claimed is:

1. A method for suppressing a progression of vascular dementia, comprising administering a therapeutically effective amount of one or more compounds selected from the group consisting of ethoxyquin and methyldopa to a subject in need thereof, wherein a dosage of methyldopa and ethoxyquin are each in a range from 0.001 to 50 mg/kg weight per day.

2. The method for suppressing the progression of the vascular dementia according to claim 1, wherein the subject is a mammal.

3. The method for suppressing the progression of the vascular dementia according to claim 1, wherein the subject is a human.

4. The method for suppressing the progression of the vascular dementia according to claim 1, wherein the subject suffers from early-onset dementia.

5. The method for suppressing the progression of vascular dementia according to claim 1, comprising administering to a subject in need thereof a food or beverage containing a therapeutically effective amount of one or more compounds selected from the group consisting of ethoxyquin and methyldopa.

6. The method of claim 5, wherein the dosage of methyldopa and ethoxyquin are each in a range from 0.1 to 50 mg/kg weight per day.

7. The method of claim 5, wherein the ethoxyquin or the methyldopa is administered once per day, or a plural times per day, or is administered once or a plural times within several days or several weeks.

8. The method of claim 1, wherein the dosage of methyldopa and ethoxyquin are each in a range from 0.1 to 50 mg/kg weight per day when administered orally or intraperitoneally.

9. The method of claim 8, wherein the dosage of methyldopa and ethoxyquin are each in a range from 0.2 to about 10 mg/kg weight per day.

10. The method of claim 9, wherein the dosage of methyldopa and ethoxyquin are each in a range from 0.3 to about 2 mg/kg weight per day.

11. The method of claim 10, wherein the dosage of methyldopa and ethoxyquin are each in a range from 0.4 to about 1 mg/kg weight per day.

12. The method of claim 1, wherein the ethoxyquin or the methyldopa is administered once per day, or a plural times per day, or is administered once or a plural times within several days or several weeks.

* * * * *